US00PP36054P2

(12) United States Plant Patent
Sakazaki

(10) Patent No.: US PP36,054 P2
(45) Date of Patent: Jul. 30, 2024

(54) ***CALIBRACHOA* PLANT NAMED 'WNCALSBBL24'**

(50) Latin Name: ***Calibrachoa* sp.**
Varietal Denomination: WNCALSBBL24

(71) Applicant: Ushio Sakazaki, Shiga (JP)

(72) Inventor: Ushio Sakazaki, Shiga (JP)

(73) Assignee: WINGEN, LLC, Mustang Ridge, TX (US)

( * ) Notice: Subject to any disclaimer, the term of this patent is extended or adjusted under 35 U.S.C. 154(b) by 24 days.

(21) Appl. No.: 18/237,591

(22) Filed: Aug. 24, 2023

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct *Calibrachoa* plant named 'WNCALSBBL24', characterized by its compact, upright to outwardly spreading and mounding to trailing plant habit; moderately vigorous growth habit; freely branching habit; dense and bushy appearance; early and freely flowering habit; relatively large dark purple-colored flowers with darker purple-colored centers and venation and bright yellow-colored throats; and excellent container and garden performance.

2 Drawing Sheets

Figure 1:
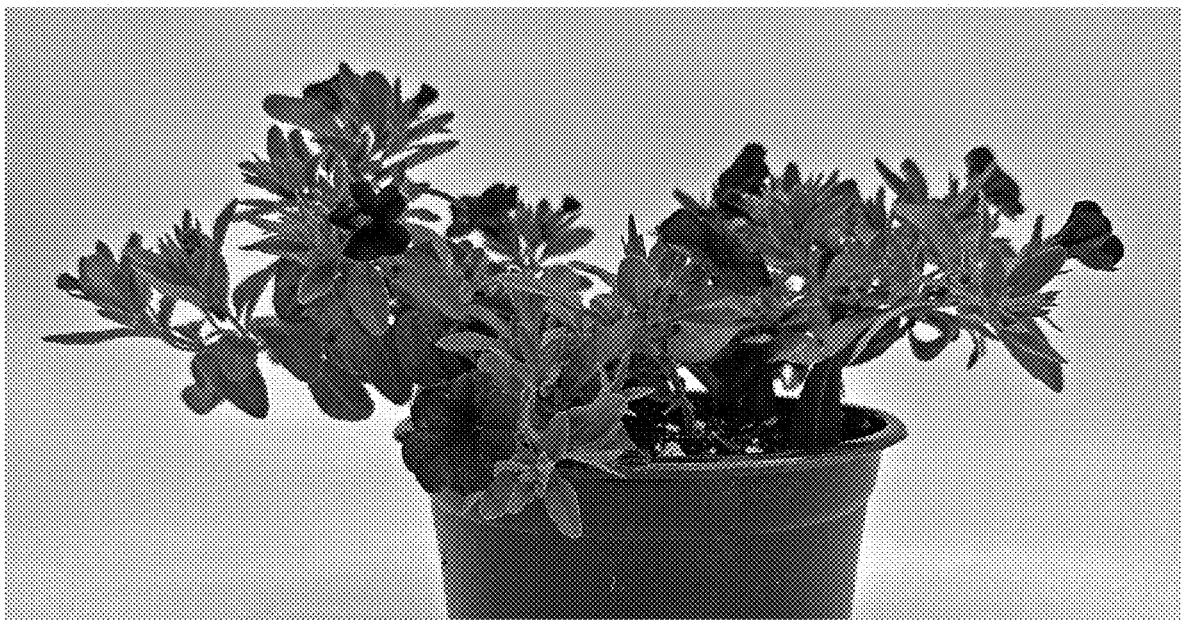

Botanical designation: *Calibrachoa* sp.
Cultivar denomination: 'WNCALSBBL24'.

BACKGROUND OF THE INVENTION

The present invention relates to a new and distinct cultivar of *Calibrachoa* plant, botanically known as *Calibrachoa* sp. and hereinafter referred to by the name 'WNCALSBBL24'.

The new *Calibrachoa* plant is a product of a planned breeding program conducted by the Inventor in Higashiomi, Shiga, Japan and Bonsall, California. The objective of the breeding program is to create new compact, uniform, freely-branching and freely-flowering *Calibrachoa* plants with unique and attractive flowers and good container and garden performance.

The new *Calibrachoa* plant originated from a cross-pollination conducted by the Inventor in Higashiomi, Shiga, Japan on May 18, 2019 of a proprietary seedling selection of *Calibrachoa* sp. identified as code number 19CJ25, not patented, as the female, or seed, parent with a proprietary seedling selection of *Calibrachoa* sp. identified as code number 16C834-03, not patented, as the male, or pollen, parent. The new *Calibrachoa* plant was discovered and first selected by the Inventor as a single flowering plant within the progeny of the stated cross-pollination in a controlled greenhouse environment in Bonsall, California on Jun. 1, 2020.

Asexual reproduction of the new *Calibrachoa* plant by vegetative terminal cuttings in a controlled greenhouse environment in Bonsall, California since Jun. 3, 2020 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNCALSBBL24'. These characteristics in combination distinguish 'WNCALSBBL24' as a new and distinct *Calibrachoa* plant:

1. Compact, upright to outwardly spreading and mounding to trailing plant habit.
2. Moderately vigorous growth habit.
3. Freely branching habit; dense and bushy appearance.
4. Early and freely flowering habit.
5. Relatively large dark purple-colored flowers with darker purple-colored centers and venation and bright yellow-colored throats.
6. Excellent container and garden performance.

Plants of the new *Calibrachoa* differ primarily from plants of the female parent selection in the following characteristics:

1. Plants of the new *Calibrachoa* are more compact than plants of the female parent selection.
2. Plants of the new *Calibrachoa* are not as vigorous as plants of the female parent selection.
3. Plants of the new *Calibrachoa* are more mounding and denser than and not as spreading and open as plants of the female parent selection.

Plants of the new *Calibrachoa* differ primarily from plants of the male parent selection in the following characteristics:

1. Plants of the new *Calibrachoa* are not as compact as plants of the male parent selection.
2. Flowers of plants of the new *Calibrachoa* are more open and flatter than and not as closed and puckered as flowers of plants of the male parent selection.

3. Plants of the new *Calibrachoa* and the male parent selection differ in flower color as flowers of plants of the new *Calibrachoa* are dark purple in color whereas flowers of plants of the male parent selection are magenta in color.

Plants of the new *Calibrachoa* can be compared to plants of the *Calibrachoa* sp. 'USCALI51', disclosed in U.S. Plant Pat. No. 14,874. In side-by-side comparisons, plants of the new *Calibrachoa* differ primarily from plants of 'USCALI51' in the following characteristics:

1. Plants of the new *Calibrachoa* are more compact and denser than and not as open as plants of 'USCALI51'.
2. Plants of the new *Calibrachoa* are not as vigorous as plants of 'USCALI51'.
3. Plants of the new *Calibrachoa* flower earlier than plants of 'USCALI51'.
4. Plants of the new *Calibrachoa* and 'USCALI51' differ in flower color as flowers of plants of the new *Calibrachoa* are dark purple in color whereas flowers of plants of 'USCALI51' are violet in color.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet (FIG. 1) is a side perspective view of a typical flowering plant of 'WNCALSBBL24' grown in a container.

Figure 2:
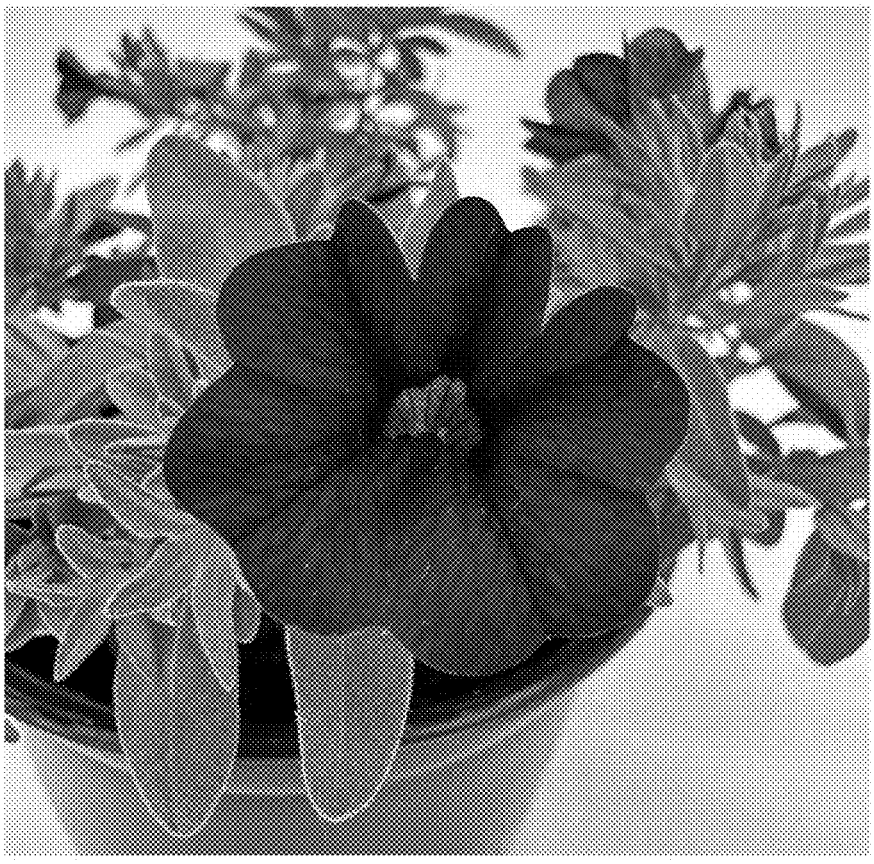

The photograph on the second sheet (FIG. 2) is a close-up view of a typical flowering plant of 'WNCALSBBL24'.

DETAILED BOTANICAL DESCRIPTION

The aforementioned photographs and following observations and measurements describe plants grown during the spring in 723-ml containers in a glass-covered greenhouse in Loudon, New Hampshire and under cultural practices typical of commercial *Calibrachoa* production. During the production of the plants, day and night temperatures averaged 20 C. Plants were seven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Calibrachoa* sp. 'WNCALSBBL24'.

Parentage:

*Female, or seed, parent*.—Proprietary seedling selection of *Calibrachoa* sp. identified as code number 19CJ25, not patented.

*Male, or pollen, parent*.—Proprietary seedling selection of *Calibrachoa* sp. identified as code number 16C834-03, not patented.

Propagation:

*Type*.—By vegetative terminal cuttings.

*Time to initiate roots, summer*.—About five to seven days at ambient temperatures about 28 C.

*Time to initiate roots, winter*.—About seven to ten days at ambient temperatures about 20 C.

*Time to produce a rooted plant, summer*.—About four to five weeks at ambient temperatures about 28 C.

*Time to produce a rooted plant, winter*.—About five to six weeks at ambient temperatures about 20 C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, upright to outwardly spreading and mounding to eventually trailing plant habit; freely branching habit with about seven to eight primary lateral branches with secondary laterals developing potentially at every node, dense and bushy plant form; pinching enhances development of lateral branches; moderately vigorous growth habit and rapid growth rate.

*Plant height*.—About 12.5 cm.

*Plant diameter*.—About 31 cm.

Lateral branch description:

*Length*.—About 12.5 cm.

*Diameter*.—About 2 mm.

*Internode length*.—About 9 mm to 10 mm.

*Strength*.—Moderately strong, flexible and sturdy.

*Aspect*.—About 45 to 90 degrees from stem axis.

*Texture and luster*.—Densely pubescent; pubescence, minute; matte to slightly glossy.

*Color, developing*.—Close to N144C.

*Color, developed*.—Close to 144A.

Leaf description:

*Arrangement*.—Alternate, simple.

*Length*.—About 4.3 cm.

*Width*.—About 1.2 cm to 1.4 cm.

*Shape*.—Narrowly elliptic.

*Apex*.—Broadly acute.

*Base*.—Cuneate to attenuate.

*Margin*.—Entire.

*Texture and luster, upper and lower surfaces*.—Sparsely pubescent; pubescence, minute; matte to slightly glossy.

*Venation pattern*.—Pinnate; arcuate.

*Color*.—Developing leaves, upper surface: Close to 144A. Developing leaves, lower surface: Close to 144A. Fully expanded leaves, upper surface: Close to between 144A and 146A; venation, close to 144A. Fully expanded leaves, lower surface: Close to 144A; venation, close to 144B.

*Petioles*.—Length: About 6.5 mm. Diameter: About 2 mm. Strength: Moderately strong, flexible. Texture and luster, upper and lower surfaces: Sparsely pubescent; pubescence, minute; matte to slightly glossy. Color, upper surface: Close to 144A. Color, lower surface: Close to 144B.

Flower description:

*Flower type and flowering habit*.—Single salverform flowers arising from leaf axils; freely flowering habit with typically about 78 flowers and flower buds developing per plant at one time; flowers face upright to outwardly.

*Fragrance*.—None detected.

*Natural flowering season*.—Plants of the new *Calibrachoa* begin flowering about five weeks after planting; plants flower continuously from the spring though the summer until frost.

*Flower longevity*.—Depending on temperature, about one to two weeks; flowers persistent.

*Flower buds, before showing petal color*.—Length: About 1 cm. Diameter: About 2.5 mm. Shape: Oblong, elongate. Texture and luster: Sparsely to moderately pubescent; pubescence, minute; matte. Color: Close to 144A to 144B.

*Flower diameter*.—About 3.4 cm by 3.5 cm.

*Flower length* (*height*).—About 2.1 cm.

*Flower throat diameter*.—About 5 mm by 7.5 mm.

*Flower tube length*.—About 1.4 cm.

*Flower tube diameter, proximally*.—About 2 mm.

*Corolla*.—Arrangement: Five fused petals opening into a flared trumpet. Petal lobe length (from throat): About 1.3 cm to 1.5 cm. Petal lobe width: About 1.7 cm to 1.8 cm. Petal shape: Fan-shaped with slight cordate tendencies. Petal apex: Rounded to shallowly retuse; slightly recurving with development. Petal margin: Entire; slightly undulate. Petal texture and luster, upper surface: Smooth, glabrous; velvety; matte. Petal texture and luster, lower surface: Mostly smooth and glabrous with sparse pubescence along midvein; slightly glossy. Throat texture and luster: Smooth, glabrous; slightly glossy. Tube texture and luster: Moderately pubescent; matte. Color: Petal lobe, when opening, upper surface: Closest to 83A. Petal lobe, when opening, lower surface: Closest to 83B to 83C. Petal lobe, fully opened, upper surface: Closest to 83A; towards the throat, close to N92A; primary venation, close to N92A, and lateral venation, close to 83A; colors do not change with subsequent development. Petal lobe, fully opened, lower surface: Closest to 83B to 83C; primary venation, close to 83A, and lateral venation, close to 83B to 83C; colors do not change with subsequent development. Throat: When opening, close to between N144A and 154A and becoming closer to 6A with flower development; venation, when opening, close to 146A and becoming closer to 6A with flower development. Tube: Close to 154C to 154D; venation, close to 154C to 154D.

*Calyx*.—Arrangement: One star-shaped calyx tube with five sepals fused towards the base and arranged in a single whorl; sepals flaring outwardly and reflexing towards the apex. Length: About 1.7 cm. Diameter: About 1.2 cm. Sepal length: About 1.7 cm. Sepal width: About 3 mm. Sepal shape: Narrowly lanceolate to linear. Sepal apex: Acute. Sepal margin: Entire. Sepal texture and luster, upper and lower surfaces: Moderately pubescent; pubescence, minute; matte. Sepal color, upper and lower surfaces: Close to 144A to 144B.

*Peduncles*.—Length: About 1.75 cm. Diameter: About 1 mm. Angle: About 45 to 60 degrees from stem axis. Strength: Moderately strong, wiry and flexible. Texture and luster: Moderately pubescent; pubescence, minute; matte to slightly glossy. Color: Close to 144A and 144B.

*Reproductive organs*.—Stamens: Quantity: Five per flower. Filament length: About 6 mm. Filament color: Close to 157C to 157D. Anther size: About 1 mm by 1 mm. Anther shape: Round. Anther color: Close to 6A. Pollen amount: None observed. Pistils: Quantity: One per flower. Pistil length: About 1 cm. Style length: About 8 mm. Style color: Close to 144B. Stigma diameter: About 1 mm. Stigma shape: Round. Stigma color: Close to 144A and 146A. Ovary color: Close to 144A.

*Seeds and fruits*.—To date, seed and fruit development have not been observed on plants of the new *Calibrachoa*.

Garden performance: Plants of the new Petunia have been observed to have excellent garden performance and have been observed to tolerate rain, wind and temperatures ranging from about 1 C to about 35 C.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'WNCALSBBL24' as illustrated and described.

* * * * *